United States Patent [19]
Rühl et al.

[11] Patent Number: 5,689,017
[45] Date of Patent: Nov. 18, 1997

[54] PREPARATION OF A MONOLITHIUM ACETYLIDE/AMMONIA COMPLEX

[75] Inventors: Thomas Rühl, Frankenthal; Rolf Müller, Hockenheim; Jochem Henkelmann, Mannheim; Marc Heider, Neustadt, all of Germany

[73] Assignee: BASF Aktiengesellschaft, Ludwigshafen, Germany

[21] Appl. No.: 542,188

[22] Filed: Oct. 12, 1995

[30] Foreign Application Priority Data

Oct. 13, 1994 [DE] Germany .................. 44 36 498.9

[51] Int. Cl.$^6$ .................................................. C07C 33/04
[52] U.S. Cl. .................. 568/874; 260/665 R; 564/509; 568/813
[58] Field of Search .................. 260/665 R; 564/488, 564/509; 568/813, 874

[56] References Cited

U.S. PATENT DOCUMENTS

| | | | |
|---|---|---|---|
| 3,441,621 | 4/1969 | Tedeschi et al. | 260/665 R |
| 3,445,534 | 5/1969 | Bach et al. | 260/665 R |
| 4,320,236 | 3/1982 | Wiederkehr . | |
| 5,068,368 | 11/1991 | Smith | 260/665 R X |

FOREIGN PATENT DOCUMENTS 642 936  5/1984  Switzerland .

OTHER PUBLICATIONS

Chimia 40 (1986) 323.

*Primary Examiner*—Paul F. Shaver
*Attorney, Agent, or Firm*—Keil & Weinkauf

[57] ABSTRACT

Preparation of a monolithium acetylide/ammonia complex by the reaction of lithium amide and acetylene in ammonia, by carrying out the reaction at a temperature of from −10° to 30° C.

5 Claims, No Drawings

PREPARATION OF A MONOLITHIUM ACETYLIDE/AMMONIA COMPLEX

The present invention relates to an improved process for the preparation of a monolithium acetylide/ammonia complex by the reaction of lithium amide and acetylene in ammonia. It also relates to the use of the acetylide complex thus prepared for the ethynylation of $\alpha,\beta$-unsaturated ketones and aldehydes.

CH-A 642,936 describes the preparation of a monolithium acetylide/ammonia complex of lithium amide and acetylene. Lithium amide is suspended in an inert organic solvent and admixed with acetylene at a temperature below 30° C. and preferably below 10° C. This manufacturing method is not completely satisfactory, since dilithium acetylide (lithium carbide) forms in the organic solvents, which is non-reactive and precipitates from the solution. Furthermore, the reaction times are relatively long. In addition, the lithium amide reacts incompletely under the conditions cited, which can lead to undesirable polymerisation thereof in subsequent reactions with $\alpha,\beta$-unsaturated carbonyl compounds.

Chimia 40 (1986) 323 discloses that the monolithium acetylide/ammonia complex is not thermally stable and decomposes in lithium carbide, acetylene, and ammonia.

It was the object of the invention to provide a process that avoids the said disadvantages of the known processes.

Accordingly, we have found the process defined above, which is characterized in that the reaction is carried out at a temperature of from −10° C. to 30° C.

The end product of the process of the invention is probably the complex $LiC{\equiv}CH.NH_3$.

According to the invention lithium amide is caused to react with acetylene. Lithium amide is obtainable as a commercial product or can be prepared, for example, by the reaction of lithium hydride with ammonia with elimination of hydrogen. The acetylene to be used in the present invention is preferably free from acetone, in order to prevent undesirable side reactions. It can be diluted with inert gases such as nitrogen or argon; it is preferably used undiluted, however.

In general, from 1 to 10 mol of acetylene can be used per mole of lithium amide, but from 1 to 3 mol are preferred.

The process according to the invention is carried out in ammonia acting as solvent. From 7 to 30 mol of ammonia are usually employed per mole of lithium amide.

In a preferred embodiment, lithium amide is initially mixed with ammonia. Then acetylene is added with stirring to form the reaction batch.

Since the acetylene dissolves and reacts relatively quickly in the ammonia, it can be added at such a rate that the pressure remains virtually constant during addition of the acetylene. It has been found to be advantageous to carry out the reaction under the autogenous pressure of the ammonia at the reaction temperature used, which corresponds, depending on the temperature of reaction, to a pressure of from ca 3 to 15 bar.

The temperature of reaction is from −10° to 30° C., preferably from 0° to 20° C.

The process according to the invention can be carried out in stirred boilers or pressure vessels.

The reaction to form the monolithium acetylide/ammonia complex is usually complete after a few minutes. It has been found to be advantageous to prepare such solutions of the acetylide complex which are approximately mono- to tri-molar solutions of the end product.

The process according to the invention allows for a virtually quantitative acetylene conversion, no lithium carbide being found as by-product. It is technically extremely desirable to allow the reaction to take place at the temperatures stated, since no expensive refrigerators are necessary in such cases. If the process is to be carried out at temperatures below room temperature, these temperatures can be established in a simple manner using brine refrigerants such as are normally present in chemical works.

The monolithium acetylide/ammonia complex prepared according to the invention can be caused to react further in conventional manner. The ammonia solution containing the complex can be depressurized with evaporation of the ammonia. The complex thus obtained can then be taken up in an inert organic solvent such as toluene, tetrahydrofuran, or methyl-tert-butyl ether and caused to react with $\alpha,\beta$-unsaturated aldehydes or ketones such as methyl vinyl ketone or acetone causing the addition of the acetylide group. Following hydrolytic purification, there are thus obtained valuable intermediates for carotenoid syntheses (cf CH-A 642,936).

EXAMPLES

Example 1

In an autoclave having a capacity of 150L (pressure rating 25 bar) there were introduced initially 8 kg of lithium amide (348 mol) and then 100L of liquid ammonia. A pressure of ca 8 bar built up.

8 $m^3$ of acetylene (357 mol) were forced into the batch with stirring. After a period of 15 min, the autoclave was depressurized and the resulting monolithlure acetylide/ammonia complex was suspended in 100L of methyl-tert-butyl ether. Lithium carbide could not be found.

At a temperature of −5° C. there were then added to the suspension 22.5 kg of methyl vinyl ketone. Following hydrolysis and distillation there was obtained 3-hydroxy-3-methyl-penten-4-in-1 in a yield of 87%.

Example 2

In a manner similar to that described in Example 1, the synthesis of the monolithium acetylide/ammonia complex was carried out at a temperature of 0° C. and an autogenous pressure of 2.5 bar.

The subsequent reaction with methyl vinyl ketone gave a yield of 89%.

Example 3

The monolithium acetylide/ammonia complex was prepared in a manner similar to that described in Example 1.

The subsequent reaction with 20.3 kg of acetone (350 mol) gave 98% of methyl butynol.

Example 4

The monolithium acetylide/ammonia complex was prepared in a manner similar to that described in Example 1.

The subsequent reaction with 70.7 kg of β-ions (350 mol) gave 94% of ethynylated ions.

We claim:

1. A process for the preparation of an ammonia solution of a monolithium acetylide/ammonia complex which comprises: reacting lithium amide and acetylene in ammonia in a pressure vessel at a temperature of from −10° to 30° C. under the autogenous pressure of the ammonia.

2. A process as defined in claim 1, wherein the reaction is carried out at a temperature of from 0° to 20° C.

3. A process as defined in claim 1, wherein the ammonia solution containing the monolithium acetylide/ammonia complex is depressurized with evaporation of the ammonia and the complex thus obtained is suspended in an inert organic solvent.

4. A process as defined in claim 3, wherein the inert organic solvent is toluene, tetrahydrofuran or methyl-tert-butylether.

5. A process as defined in claim 3, wherein the suspension of the complex in the inert organic solvent is reacted with $\alpha,\beta$-unsaturated aldehyde or ketone in order to ethynylate said aldehyde or ketone.

* * * * *